United States Patent [19]
Haraguchi

[11] Patent Number: 5,833,606
[45] Date of Patent: Nov. 10, 1998

[54] NONCONTACT TONOMETER FOR MEASURING INTRAOCULAR PRESSURE

[75] Inventor: Tsuyoshi Haraguchi, Tokyo, Japan

[73] Assignee: Kabushiki Kaisha TOPCON, Tokyo, Japan

[21] Appl. No.: 842,014

[22] Filed: Apr. 23, 1997

[30] Foreign Application Priority Data

Apr. 24, 1996 [JP] Japan .................................... 8-102623

[51] Int. Cl.$^6$ ........................................................ A61B 3/16
[52] U.S. Cl. ............................................ 600/401; 600/405
[58] Field of Search ...................................... 600/398, 401, 600/403, 405, 406; 73/78, 79, 81

[56] References Cited

U.S. PATENT DOCUMENTS

| | | | |
|---|---|---|---|
| 4,996,990 | 3/1991 | Hideshima | 600/401 |
| 5,002,056 | 3/1991 | Takahashi et al. | 600/405 |
| 5,107,851 | 4/1992 | Yano et al. | 600/405 |
| 5,279,300 | 1/1994 | Miwa et al. | 600/401 |
| 5,523,808 | 6/1996 | Kohayakawa | 600/401 |

*Primary Examiner*—Jennifer Bahr
*Assistant Examiner*—Bryan K. Yarnell
*Attorney, Agent, or Firm*—Finnegan, Henderson, Farabow, Garrett & Dunner, L.L.P.

[57] ABSTRACT

A noncontact tonometer for measuring intraocular pressure is provided. When a rotary solenoid (7) is supplied with electric power, a piston (4) within a cylinder (2) is moved up, and thereby air is jetted through a nozzle (9) of a head (3) toward an eye (H) of a subject. At the same time, infrared rays are projected onto the eye (H) from a light source (11). Reflected light from a cornea of the eye (H) is received by a light receiving sensor (12). A signal generated by the light receiving sensor (12) is transmitted to a control circuit (16) via a flat-state detecting circuit (13). As a result, the intraocular pressure of the eye (H) is measured. The noncontact tonometer further includes two condensers (17, 18). A command from the control circuit (16) is input to a condenser switching portion (20) by operating a driving switch (21). Thereby, one of the condensers (17, 18) is selected to supply the rotary solenoid (7) with the electric power.

6 Claims, 4 Drawing Sheets

NONCONTACT TONOMETER FOR MEASURING INTRAOCULAR PRESSURE

BACKGROUND OF THE INVENTION

1. Field of the Invention

This invention relates to a noncontact tonometer that measures intraocular pressure of an eye of a subject while jetting a fluid against a cornea of the eye.

2. Description of the Related Art

In a conventional noncontact tonometer, a beam of light is projected onto a cornea of a subject's eye while a fluid is being jetted against the cornea so as to deform the cornea. The quantity of light reflected by the cornea is detected at this time, and the intraocular pressure of the eye is measured. In this noncontact tonometer, in most cases, air is used as a fluid to be jetted against the cornea. The air is compressed by a piston sliding within a cylinder and is jetted from a nozzle toward the eye in pulses.

Generally, the noncontact tonometer is provided with a condenser and a rotary solenoid. The rotary solenoid is supplied with electric energy from the condenser and is actuated so that the piston is reciprocated.

However, this conventional noncontact tonometer includes only one condenser for actuating the solenoid. For this reason, after a first measurement of the intraocular pressure is completed, several seconds to ten-odd seconds are consumed until the next measurement thereof is ready to be made. After discharging electric energy completely, the condenser requires several seconds to ten-odd seconds to again obtain a full charge of electricity. An operator must wait during this period.

In addition, the conventional noncontact tonometer has no display means for showing waiting time required for the next measurement. Therefore, there is a fear that the operator will wait for a long while without doing anything.

SUMMARY OF THE INVENTION

It is therefore an object of the present invention to provide an easily operated noncontact tonometer which is capable of making the present measurement of intraocular pressure of an eye soon after the preceding measurement of it is completed and which includes a display means for displaying waiting time for the next measurement.

In order to achieve the object, according to an aspect of the present invention, in a noncontact tonometer that measures intraocular pressure of an eye of a subject by detecting deformation of a cornea of the eye while jetting a fluid through a nozzle toward the cornea, the noncontact tonometer comprises a plurality of energy storing means filled with electric energy; a fluid jetting means for jetting a fluid through the nozzle in pulses by obtaining the electric energy from the energy storing means; and an energy supply switching means for supplying the fluid jetting means with the electric energy stored in the energy storing means such that the fluid jetting means is alternately connected to any one of the plurality of energy storing means switched over whenever measurement instructions are input.

Since the plurality of energy storing means are provided as recited above, the fluid jetting means is shifted and connected to the other energy storing means by the energy supply switching means when one of the plurality of energy storing means has used up all the electric energy. Accordingly, the fluid jetting means is supplied with electric energy from the other energy storing means. This makes it possible to continuously jet a fluid in spite of the fact that the fluid jetting means has already jetted a fluid. Therefore, time from the present measurement to the next measurement can be shortened. The energy storing means that has discharged all the electric energy is recharged while the energy storing means has no connection with the fluid jetting means, in other words, while the other energy storing means is in connection with the fluid jetting means.

According to another aspect of the present invention, in a noncontact tonometer that measures intraocular pressure of an eye of a subject by detecting deformation of a cornea of the eye while jetting a fluid through a nozzle onto the cornea, the noncontact tonometer comprises an energy storing means filled with electric energy; a fluid jetting means for jetting a fluid through the nozzle in pulses by obtaining the electric energy from the energy storing means; a calculation means for calculating waiting time from time when the energy storing means is fully charged with the electric energy to time when the next measurement of the intraocular pressure of the eye is ready to be made; and a display means for displaying the waiting time that has been calculated.

Since there is known a period between the time when the energy storing means has discharged all the stored electric energy and the time when the identical energy storing means is fully recharged, the calculation means can, based on the known period, calculate time to wait until the next measurement is ready to be made. The waiting time can be also calculated in such a way that a charged state of the energy storing means charged with electric energy is first detected, charging time required for charging the energy storing means with electric energy is then calculated based on a result of the charged state, and waiting time is calculated based on the charging time. Additionally, since the calculated waiting time is displayed on the monitor or the like, the operator can view the waiting time displayed thereon and ascertain the time to wait until the next measurement.

A construction may be employed in which the noncontact tonometers according to the aforementioned aspects of the present invention are combined. In more detail, in a noncontact tonometer that measures intraocular pressure of an eye of a subject by detecting deformation of a cornea of the eye while jetting a fluid through a nozzle onto the cornea, the noncontact tonometer comprises a plurality of energy storing means filled with electric energy; a fluid jetting means for jetting a fluid through the nozzle in pulses by obtaining the electric energy from the energy storing means; an energy supply switching means for supplying the fluid jetting means with the electric energy stored in the energy storing means such that the fluid jetting means is alternately connected to any one of the plurality of energy storing means switched over whenever measurement instructions are input; a calculation means for calculating waiting time from time when the energy storing means are fully charged with the electric energy to time when the next measurement of the intraocular pressure of the eye is ready to be made; and a display means for displaying the waiting time that has been calculated.

DETAILED DESCRIPTION OF THE PREFERRED EMBODIMENTS

Embodiments of the present invention will be hereinafter described with reference to the attached drawings.

First Embodiment

Figure 1:
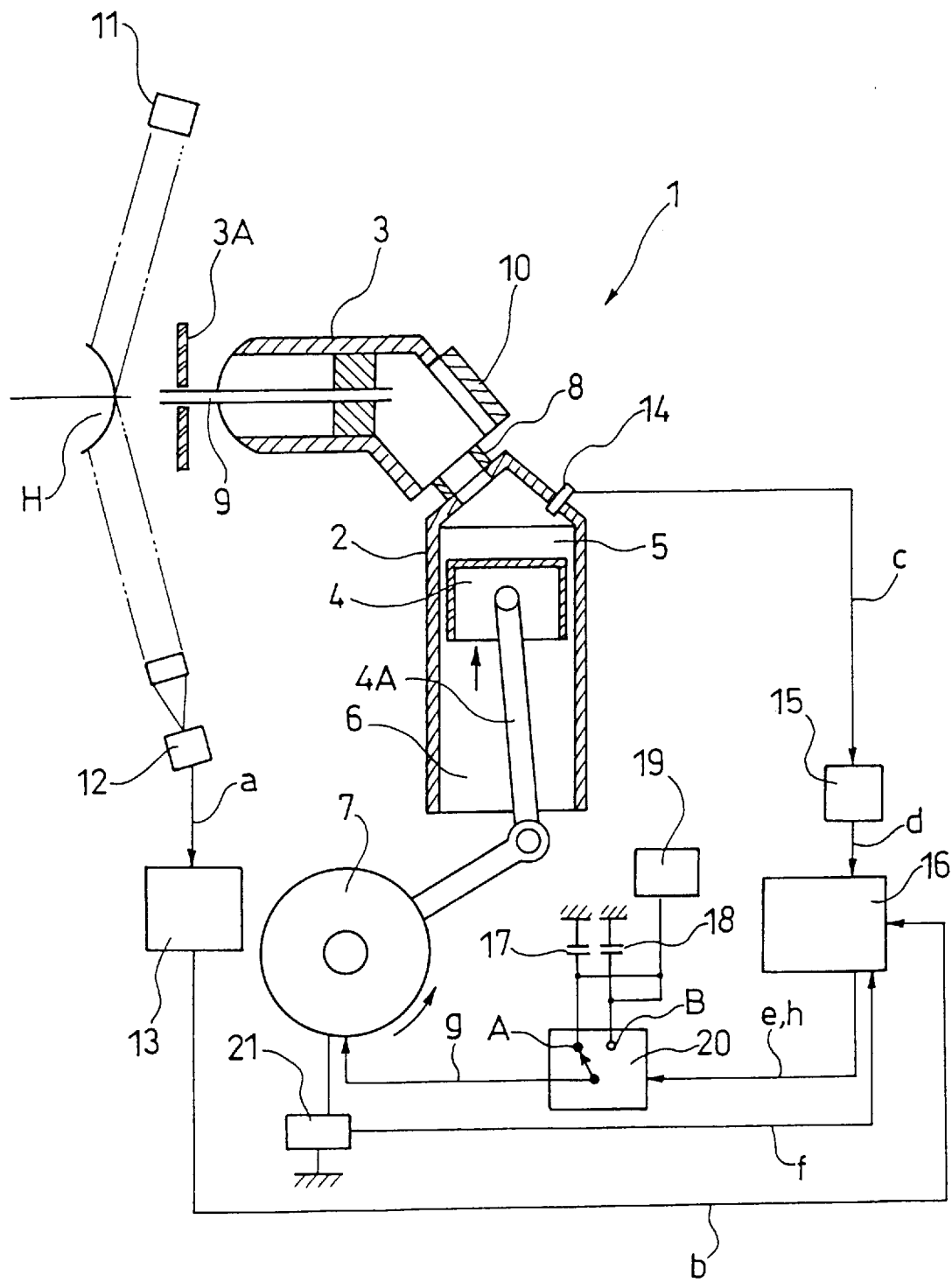
FIG. 1 is a schematic view of a noncontact tonometer according to a first embodiment of the present invention.

FIG. 1 schematically shows a noncontact tonometer according to the present invention. In FIG. 1, reference character 1 designates an air jet device. The air jet device 1 has a cylinder 2 and a head 3. A cylindrical piston 4 with a bottom is mounted in the cylinder 2. By the piston 4, the inner part of the cylinder 2 is divided into an air compressing chamber 5 and an air opening chamber 6. The piston 4 is connected to a rotary solenoid 7 via a rod 4A, and is driven by the rotation of the rotary solenoid 7. In detail, the piston 4 is moved up by the rotation of the rotary solenoid 7 when electric power is supplied to the rotary solenoid 7, whereas the piston 4 is moved down by the restitutive force of a spring (not shown) mounted in the rotary solenoid 7 when the electric power supplies thereto are cut off.

The head 3 is attached to the upper part of the cylinder 2 via a flexible tube 8 made of gum, synthetic resin, or the like. The head 3 is hollow. A nozzle 9 is attached to an end of the head 3, and is directed to an eye H of a subject. Compressed air as a measuring fluid compressed in the compressing chamber 5 within the cylinder 2 is jetted toward the eye H through the nozzle 9. Reference character 3A designates a cover glass mounted on the head 3, and reference character 10 designates a chamber window glass for an optical system.

In the vicinity of the cover glass 3A, there are disposed a light source 11 for projecting infrared rays of light onto the eye H and a light receiving sensor 12 for receiving the infrared rays which have been reflected by a cornea of the eye H. The light receiving sensor 12 is connected to a flat-state detecting circuit 13. The flat-state detecting circuit 13 detects a flat state of the cornea from a light receiving signal a output by the light receiving sensor 12 and thereafter outputs a flat-state detecting signal b.

A pressure sensor 14 is attached to a sidewall of the cylinder 2, and is connected to a pressure detecting circuit 15. Based on a detection signal c from the pressure sensor 14, the pressure detecting circuit 15 detects pressure in the compressing chamber 5 and outputs a pressure signal d. The flat-state detecting circuit 13 and the pressure detecting circuit 15 are connected to a control circuit 16 made up of a microcomputer and the like. Based on the flat-state detecting signal b from the flat-state detecting circuit 13 and the pressure signal d from the pressure detecting circuit 15, the control circuit 16 outputs a command signal e for driving and controlling the rotary solenoid 7 and calculates the intraocular pressure of the eye H.

In addition, two condensers 17, 18 are provided to supply electricity to the rotary solenoid 7. The plus terminals of the condensers 17, 18 are connected to a power source 19. When the condensers 17, 18 have dwindled in quantity of electricity, they are immediately charged with electricity from the power source 19. According to the command signal e output by the control circuit 16, a condenser switching portion 20 performs a switchover between an A-terminal and a B-terminal so as to selectively connect any one of the condensers 17, 18 to the rotary solenoid 7. A driving switch 21 outputs a driving signal f to the control circuit 16. The driving switch 21 is operated when electricity discharged from the condenser 17 or 18 is supplied to the rotary solenoid 7.

A description will now be given of operation of the thus constructed noncontact tonometer.

When the air jet device 1 is in a state of no action (i.e., when waiting the output of a command signal e), the piston 4 is in the lowest position within the cylinder 2. At this time, the light source 11 projects infrared rays onto the eye H. In this state, the driving switch 21 is turned on, and thereby a driving signal f is input to the control circuit 16. The control circuit 16 then outputs a command signal e, and the condenser switching portion 20 is operated to select, for example, the A-terminal. As a result, the condenser 17 is connected to the rotary solenoid 7. (The B-terminal may be selected to connect the condenser 18 to the rotary solenoid.)

When the condenser 17 is connected to the rotary solenoid 7, electric power g is supplied to the rotary solenoid 7 from the condenser 17, and thereby the rotary solenoid 7 rotates counterclockwise as shown by the arrow in FIG. 1. This rotation allows the piston 4 to move up as shown by the arrow in FIG. 1. As a result, air in the compressing chamber 5 is compressed and jetted toward the eye H through the nozzle 9. This air jet flattens the cornea of the eye H. The light receiving sensor 12 receives the infrared rays which have been reflected by the flattened cornea, and outputs a light receiving signal a to the flat-state detecting circuit 13. Based on the light receiving signal a, the flat-state detecting circuit 13 outputs a flat-state detecting signal b which shows the degree of flatness of the cornea. When the flat-state detecting signal b is input to the control circuit 16, the control circuit 16 outputs a stop signal h to the condenser switching portion 20 and, at the same time, stops outputting a command signal e. Thus, the electric power supplies are stopped to the rotary solenoid 7.

The piston 4 is slightly moved up by means of the force of inertia of the piston 4 itself in spite of the fact that the electric power supplies have been stopped to the rotary solenoid 7. When the piston 4 reaches the uppermost position within the cylinder 2, the piston 4 receives downward force caused by the restitutive force of the spring (not shown) in the rotary solenoid 7, and starts descending.

When performing the measurement of the intraocular pressure of the eye H while jetting the air toward the eye H, the outside air is inhaled into the inside of the cylinder 2 through the nozzle 9 in accordance with the descent of the piston 4. As a result, the piston 4 reaches the lowest position within the cylinder 2.

After that, the driving switch 21 is again operated to output a driving signal f. Thereby, a command signal e is output from the control circuit 16. This command signal e allows the condenser switching portion 20 to shift a connection of the rotary solenoid 7 from the condenser 17 to the condenser 18. The condenser 17 has discharged all the electricity at the aforementioned measurement, but the condenser 18 is full of electricity. Thus, by connecting the condenser 18 to the rotary solenoid 7, the operator can continuously make the measurement without waiting. The condenser 17 is supplied and charged with electricity while the condenser 18 is in connection with the rotary solenoid 7.

According to this embodiment, it is impossible to measure intraocular pressure of the eye H only when the two condensers 17, 18 are simultaneously charged with electricity. Except for this, the waiting time for the measurement is very short. Two condensers will answer the purpose in practice. However, three, four, or more condensers may be used if necessary, so that the waiting time is shortened even more.

Second Embodiment

Figure 2:
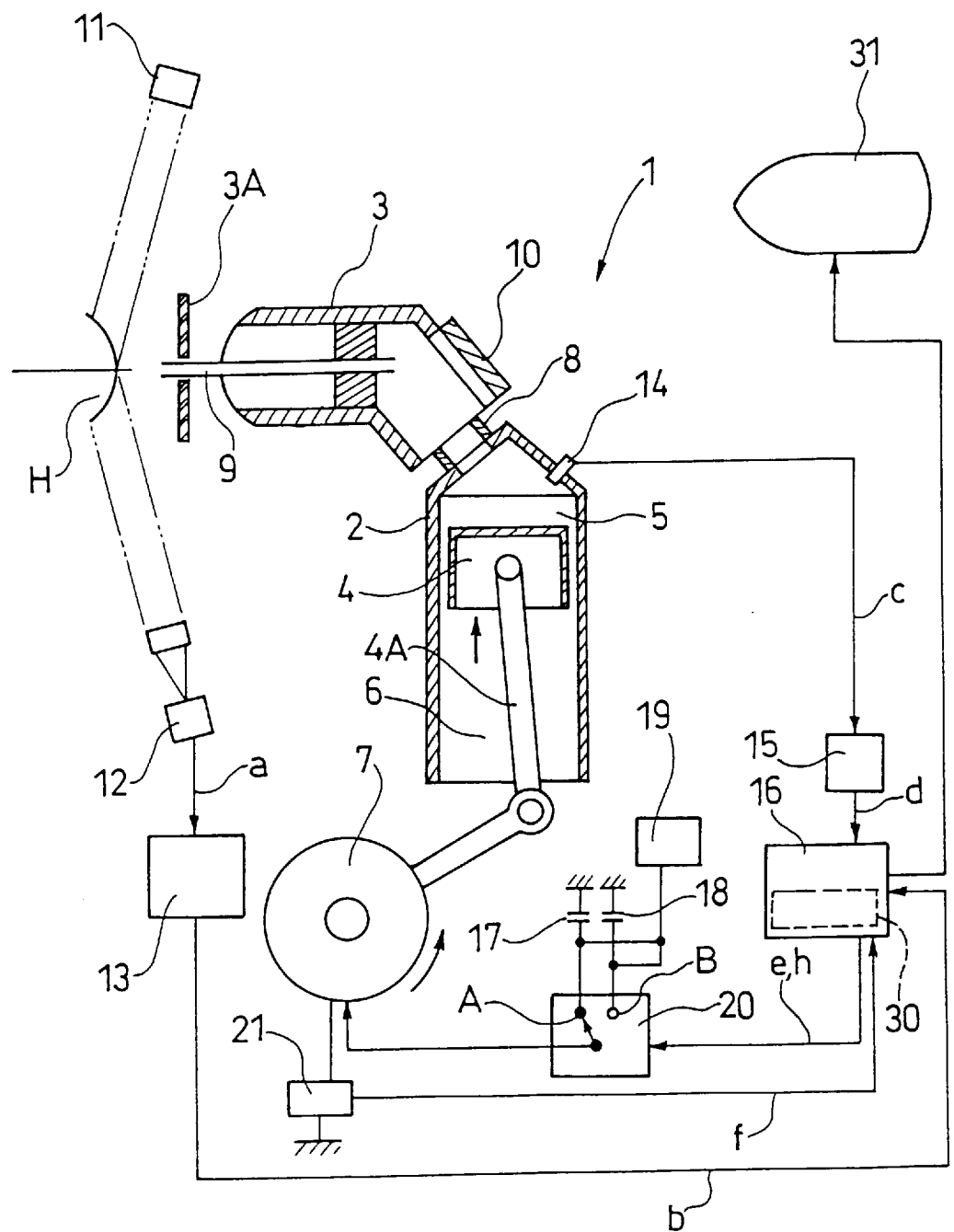
FIG. 2 is a schematic view of a noncontact tonometer according to a second embodiment of the present invention.

FIG. 2 shows a second embodiment of the present invention. A feature of the second embodiment is that the control circuit 16 is provided with a waiting-time calculating portion 30. The waiting-time calculating portion 30 serves to calculate waiting time from the time the condensers 17, 18 have reached a state of full charge to the time the next measurement is ready to be made. In addition, a monitor 31 is provided to display the waiting time.

Figure 3:
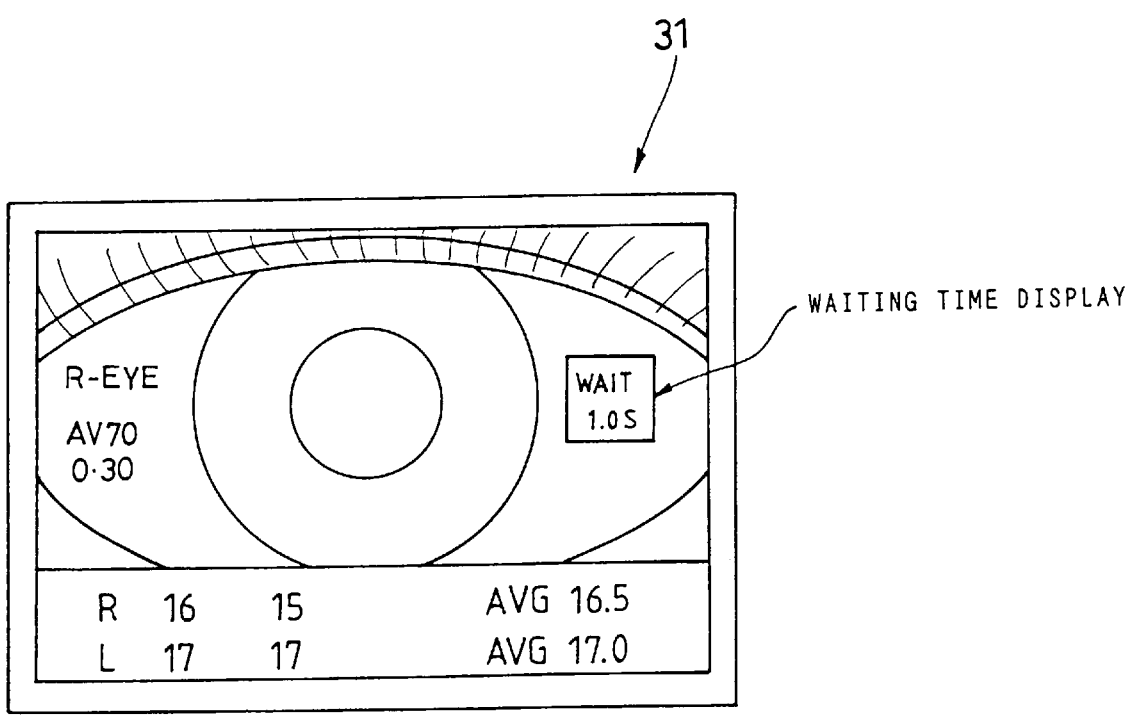
FIG. 3 shows an example in which waiting time for measurement is displayed on a monitor.
Figure 4:
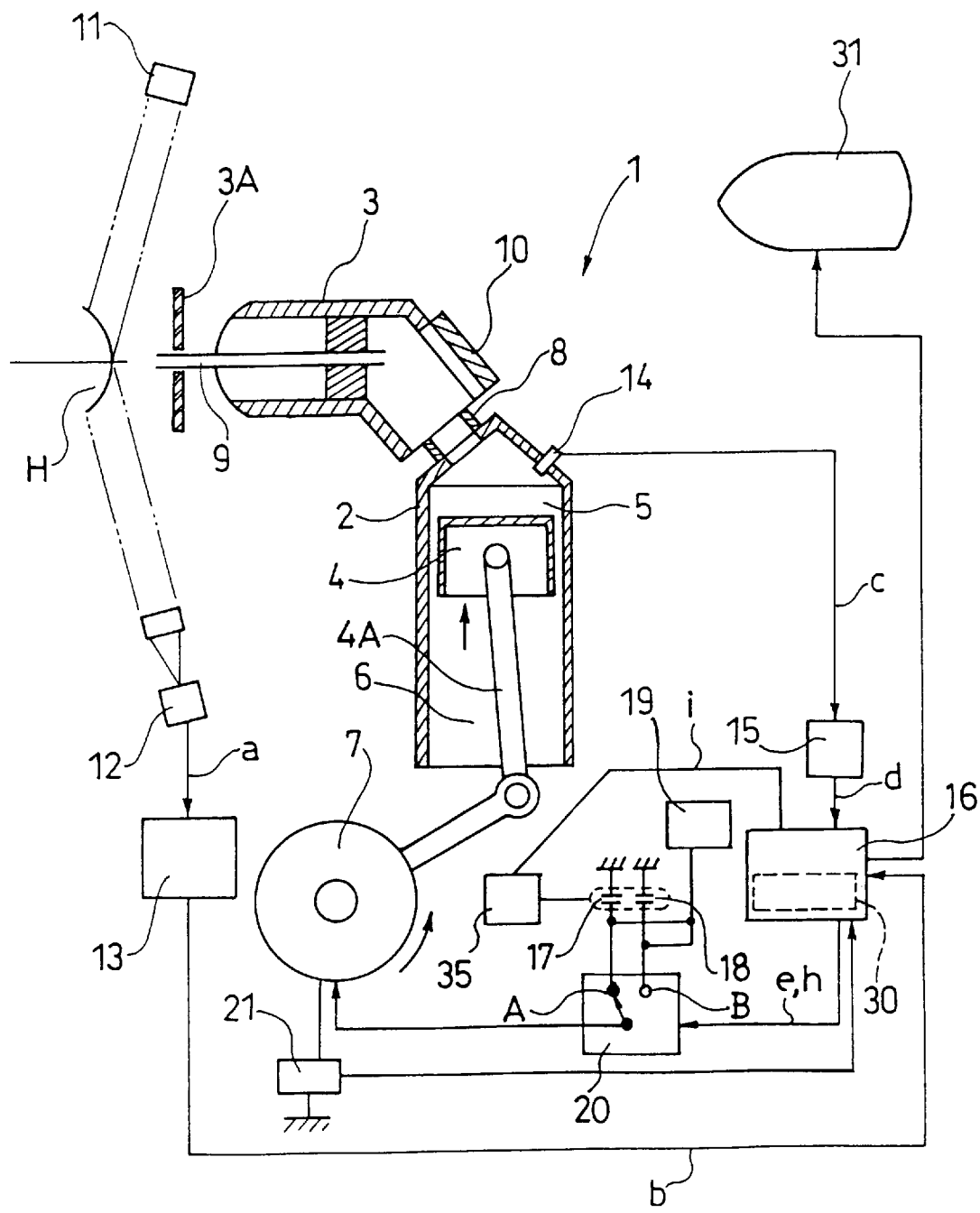
FIG. 4 is a schematic view of a noncontact tonometer according to a modification of the second embodiment of the present invention.

As described above, after the electric power supply to the rotary solenoid 7 is completed, the condenser 17 or 18 is charged with electricity from the power source 19. Generally, time required for fully charging the condenser 17 or 18 is known. Accordingly, if data about the time required for the charging is stored in the control circuit 16 beforehand, the waiting-time calculating portion 30 can, based on the data, calculate the waiting time until the next measurement. The calculated waiting time is displayed on the monitor 31 in the form of, for example, digital seconds, as shown in FIG. 3. The operator views the display and ascertains the waiting time until the next measurement. Alternatively, a charge detecting circuit 35 may be provided to detect the degree of charge of the condenser 17 or 18. If so, waiting time can be calculated based on a detection signal i output by the charge detecting circuit 35. Accordingly, time for completing the charge on the condenser 17 or 18 can be detected with satisfactory accuracy, and therefore the waiting time until the next measurement can be calculated with high accuracy.

In this embodiment, the calculated waiting time may be displayed on the monitor 31 not in a digital form but in an analog form (e.g., in the form of watch hands), or any display device other than a monitor may be used to inform the operator of the waiting time.

In the aforementioned embodiments, use is made of the two condensers 17, 18, the waiting-time calculating portion 30, and the monitor 31. However, the waiting-time calculating portion 30 and the monitor 31 are applicable to a noncontact tonometer provided with three or more condensers or are applicable to a noncontact tonometer provided with only one condenser.

What is claimed is:

1. A noncontact tonometer for measuring intraocular pressure of an eye of a subject by detecting deformation of a cornea of the eye while jetting a fluid through a nozzle onto the cornea, said noncontact tonometer comprising:
    a detection sensor for measuring the intraocular pressure;
    a control circuit connected to the detection sensor;
    a plurality of energy storing means for storing electric energy;
    fluid jetting means for jetting the fluid through the nozzle in pulses by the electric energy from said energy storing means; and
    energy supply switching means for supplying said fluid jetting means with the electric energy stored in said energy storing means such that said fluid jetting means is alternately connected to any one of the plurality of said energy storing means when a measurement command is input, the energy supply switching means being connected to the control circuit.

2. A noncontact tonometer for measuring intraocular pressure of an eye of a subject by detecting deformation of a cornea of the eye while jetting a fluid through a nozzle onto the cornea, said noncontact tonometer comprising:
    a detection sensor for measuring the intraocular pressure;
    energy storing means for storing electric energy;
    fluid jetting means for jetting the fluid through the nozzle in pulses by the electric energy from said energy storing means; and
    calculation means for calculating waiting time from a time when said energy storing means is fully charged with the electric energy to another time when a next measurement of the intraocular pressure of the eye is ready to be made, the calculation means being connected to the detection sensor; and
    display means for displaying the waiting time that has been calculated.

3. A noncontact tonometer for measuring intraocular pressure of an eye of a subject by detecting deformation of a cornea of the eye while jetting a fluid through a nozzle onto the cornea, said noncontact tonometer comprising:
    a detection sensor for measuring the intraocular pressure;
    a plurality of energy storing means for storing electric energy;
    fluid jetting means for jetting the fluid through the nozzle in pulses by the electric energy from said energy storing means; and
    energy supply switching means for supplying said fluid jetting means with the electric energy stored in said energy storing means such that said fluid jetting means is alternately connected to any one of the plurality of said energy storing means when a measurement command is input;
    calculation means for calculating waiting time from a time when said energy storing means is fully charged with the electric energy to another time when a next measurement of the intraocular pressure of the eye is ready to be made, the calculation means being connected to the detection sensor; and
    display means for displaying the waiting time that has been calculated.

4. A noncontact tonometer as recited in claim 2 or 3, wherein said calculation means beforehand stores data about time required for fully charging said energy storing means with the electric energy, and the waiting time is calculated based on said data.

5. A noncontact tonometer as recited in claim 2 or 3, wherein said calculation means detects a charged state of said energy storing means charged with the electric energy, charging time required for filling said energy storing means with the electric energy is then calculated based on a detection result of the charged state, and the waiting time is calculated based on the charging time.

6. A noncontact tonometer as recited in one of claims 1 to 3, wherein said energy storing means is a condenser.

* * * * *